United States Patent [19]

Gagne

[11] Patent Number: 4,565,561
[45] Date of Patent: Jan. 21, 1986

[54] METHOD OF AND APPARATUS FOR ANALYZING ATMOSPHERE OF A FURNACE

[75] Inventor: Robert Gagne, Cumberland, Md.
[73] Assignee: PPG Industries, Inc., Pittsburgh, Pa.
[21] Appl. No.: 678,425
[22] Filed: Dec. 5, 1984
[51] Int. Cl.⁴ .............................................. C03B 5/04
[52] U.S. Cl. ...................................... 65/135; 65/158; 65/162; 65/DIG. 13; 73/23; 422/62; 432/181; 432/182
[58] Field of Search ................. 65/158, 162, DIG. 13, 65/135; 73/23; 422/62, 111; 432/181, 182

[56] References Cited
U.S. PATENT DOCUMENTS 3,856,496 12/1974 Nesbitt et al. ..................... 65/158 X
4,338,117 7/1982 Savolskis et al. .
4,358,305 11/1982 Sleighter .

FOREIGN PATENT DOCUMENTS 143158 6/1980 German Democratic Rep. ... 65/162

OTHER PUBLICATIONS

Dr. Sam Langridge, Current Trends in Oxygen Analysis on Glass Melting Furnaces. Glass, Apr. 1984, pp. 126, 128.

Primary Examiner—Robert Lindsay
Attorney, Agent, or Firm—Robert A. Westerlund, Jr.

[57] ABSTRACT

An apparatus for monitoring a negative pressure atmosphere, e.g. a regenerative furnace atmosphere during an exhaust cycle, has aspirating facilities for aspirating an atmospheric sample from the negative pressure atmosphere and moving the sample past an analyzer for content analysis thereof.

18 Claims, 4 Drawing Figures

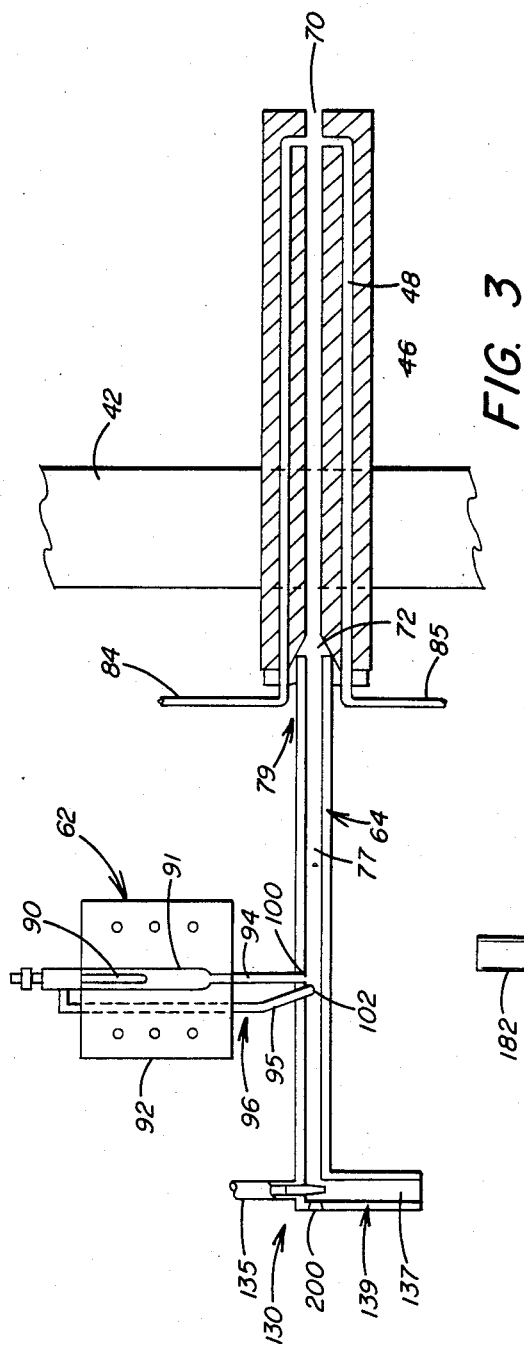
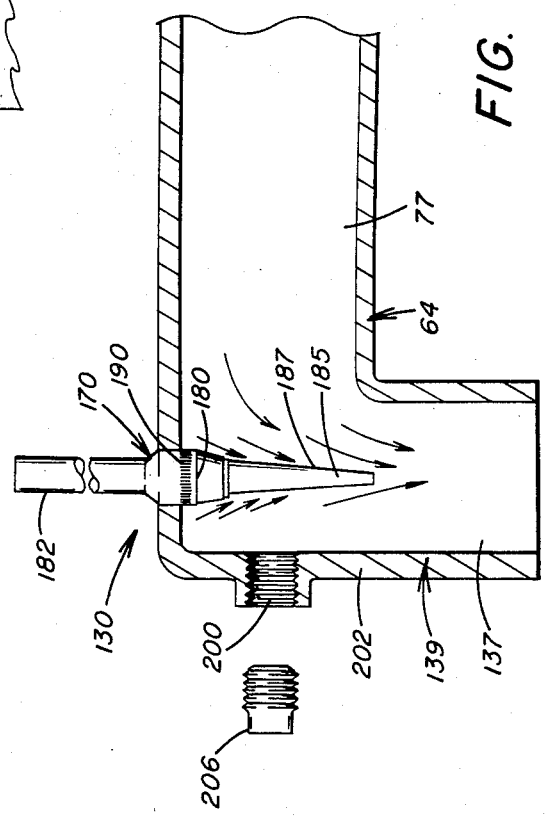

ns and width.
METHOD OF AND APPARATUS FOR ANALYZING ATMOSPHERE OF A FURNACE

FIELD OF THE INVENTION

The present invention relates to a device for and method of analyzing an atmosphere, e.g., measuring the oxygen content of the atmosphere of a regenerative furnace, e.g., such as the type used for melting and/or fining glass.

DISCUSSION OF THE TECHNICAL PROBLEMS

In the process of making a continuous flat glass ribbon, glass batch materials are conveniently moved into the upstream end of a heated combustion chamber. As the batch materials move downstream through the heated chamber, they melt to provide a pool of molten glass. The molten glass, as it advances through the heated chamber, is fined and the fined molten glass is continuously and controllably fed onto a pool of molten metal contained in a heated forming chamber. The molten glass, as it advances through the forming chamber, is controllably cooled and acted on to exit the forming chamber as a continuous glass ribbon of a given thickness and width.

The combustion chamber usually includes a regenerator at each of opposed chamber walls. The regenerators are usually elongated corridors which communicate with the chamber interior by way of a plurality of spaced ports in each of the opposed chamber walls. The interior of the regenerators usually includes a stacked arrangement of bricks, sometimes called "checker packing," which are heated by hot exhaust gases passing through the ports at one chamber wall and over the checker packing during one half of a heating cycle. During the remaining half of the heating cycle, combustion air passes over the heated checker packing through the ports past a fuel pipe mounted at the mouth of each port. The heated combustion air and combustion fuel from the pipes mix which results in flames issuing from the side of the chamber toward the chamber interior to heat same. With the above arrangement, as the packing of a regenerator at one side of the chamber is absorbing heat from the exhaust gases during one half of a heating cycle, the packing of the regenerator at the other side is heating incoming combustion air.

To maintain a high combustion efficiency and a chemical balance in the molten glass, the furnace atmosphere is monitored. In this regard, the exhaust gas is monitored to determine the percent of oxygen content therein. If the percent of oxygen content in the chamber is above a predetermined level, the combustion may be considered to be incomplete, e.g., insufficient fuel moving through the fuel pipes, and if the oxygen content is below the predetermined level, there may be too much fuel moving through the fuel pipe resulting in wasting unignited fuel. In addition to monitoring oxygen content of the chamber atmosphere to determine combustion efficiency, oxygen content in the chamber atmosphere is also monitored because it can affect the fining process. For example, excess oxygen can cause excessive bubbles in the fined molten glass which results in excess voids in the formed glass ribbon. In addition, oxygen partial pressure in the chamber can affect the color of the formed glass ribbon. By way of illustration, oxygen partial pressure may be controlled to prevent undesirable oxidation of the iron or reduction of the iron or sulfur in the molten glass which can result in a yellowish green colored glass ribbon, a bluish tint in the glass ribbon, or an amber colored glass ribbon.

There are presently available devices for monitoring the atmospheric content of the combustion chamber. These include the devices taught in U.S. Pat. No. 4,358,305 issued to Sleighter, and in U.S. Pat. No. 4,338,117 issued to Savolski and Sanders. Sleighter teaches a piping arrangement which directly interconnects the chamber atmosphere to an oxygen analyzer wherein a sample of the chamber atmosphere is continuously moved through the piping to the analyzer by the biasing action of the positive pressure differential between the chamber atmosphere and the ambient atmosphere. Although the Sleighter analyzer is acceptable, there are limitations. For example, the analyzer of Sleighter must be deployed between the ports whereat the atmospheric pressure of the furnace is positive. Since the atmosphere between the ports is an admixture of the combustion issuing from adjacent ports on opposite sides of the Sleighter device it is difficult, if not impossible, to determine from which port the combustion issued. Thus, using the Sleighter device it is difficult, if not impossible, to determine which port must have its fuel supply adjusted in response to the atmospheric content determined by the analyzer.

There also exist devices for monitoring a negative pressure zone of a furnace, such as the probe taught in U.S. Pat. No. 4,338,117 issued to Savolskis and Sanders. The Savolskis patent teaches a device having an analyzer probe directly exposed to the atmosphere of a regenerator for monitoring oxygen content thereof. However, because the Savolskis device does not draw a sample to a furnace exterior location to the analyzer, the sample it monitors is not as representative of the true atmosphere of the regenerator, due to ambient air intrusion through the regenerator walls to the regenerator interior. Furthermore, the longevity of the analyzer and sensor is decreased by exposure to the hostile regenerator atmosphere.

As can now be appreciated, it would be advantageous to provide a method of and apparatus for monitoring a combustion atmosphere that eliminates the limitations and drawbacks of the presently available techniques.

SUMMARY OF THE INVENTION

The present invention relates, in one of its aspects, to an improved furnace atmosphere sensing apparatus and especially to improvements over the device taught in U.S. Pat. No. 4,358,305 entitled "METHOD OF AND APPARATUS FOR ANALYZING ATMOSPHERE OF A COMBUSTION CHAMBER," which teachings are hereby incorporated by reference and in U.S. Pat. No. 4,388,117, entitled "ATMOSPHERE SENSING DEVICE FOR A FURNACE," which is the subject matter of U.S. Pat. No. 4,338,117, which teachings are hereby incorporated by reference.

The present invention includes a piping arrangement which is disposed in communication with a combustion atmosphere, and aspirating facilities operatively associated therewith for inducing or drawing a portion or sample of the combustion atmosphere past an analyzer which determines the oxygen and/or percent combustion products in the combustion atmosphere, the analyzer being situated exteriorly of the combustion atmosphere. The combustion atmosphere is preferably a negative pressure zone of a combustion furnace. The combustion furnace may be of the type used to melt glass batch materials and/or to fine molten glass and may be of the type used in making a continuous flat glass ribbon, e.g., a regenerative furnace having a regenerator disposed in fluid communication with opposite sides of a combustion chamber. The pressure differential between the interior atmosphere of each regenerator during its exhaust during its exhaust cycle and the ambient atmosphere is negative, and it is preferred that the apparatus of the present invention be deployed or mounted in the outside wall of either regenerator to aspirate a regenerator combustion atmosphere sample during its exhaust cycle past the analyzer disposed exteriorly of the regenerator, via the piping arrangement. The piping arrangement preferably includes a sample conduit or sample line inserted through a hole provided in the exterior wall of either regenerator, the sample line preferably extending from within the regenerator interior atmosphere to the furnace exterior or ambient atmosphere and a convection pipe loop having a sample entrance end and a sample exit end fluidly connecting the analyzer and the sample line. The aspirating facilities are disposed downstream of the exit end of the convection pipe loop for creating at least a partial vacuum within the sample line to induce a portion or sample of the regenerator interior atmosphere to flow through the sample line and the convection pipe loop past the analyzer, to have its content determined, prior to the sample exiting the sample line to the ambient atmosphere.

The present invention also relates to a method for monitoring the atmosphere of a furnace, wherein pressure differential between the furnace atmosphere being monitored and the ambient atmosphere is negative, including the steps of aspirating a portion of the furnace atmosphere to be monitored, defined as a sample, to a furnace exterior location and analyzing the sample with respect to its content. The method of this invention further includes the step of controlling the chamber atmosphere in response to the analyzing step.

BRIEF DESCRIPTION OF THE DRAWING

FIG. 3 is a view similar to the view shown in FIG. 2, except that the analyzing apparatus is mounted normal to the furnace target wall and portions are removed for illustrative clarity.

FIG. 4 is an isolation, partial cross-sectional, side elevational view of the preferred embodiment of the aspirating facilities of the present invention.

DESCRIPTION OF THE INVENTION

The present invention will be discussed in the technological environment of a regenerative flat glass melting furnace, and in conjunction with an atmospheric analyzer which functions to monitor the furnace atmosphere for oxygen and/or combustible elements content. However, it is to be understood that the present invention is not limited by the type of atmosphere being analyzed, nor by the type of analyzer employed to monitor the atmosphere.

Figure 1:
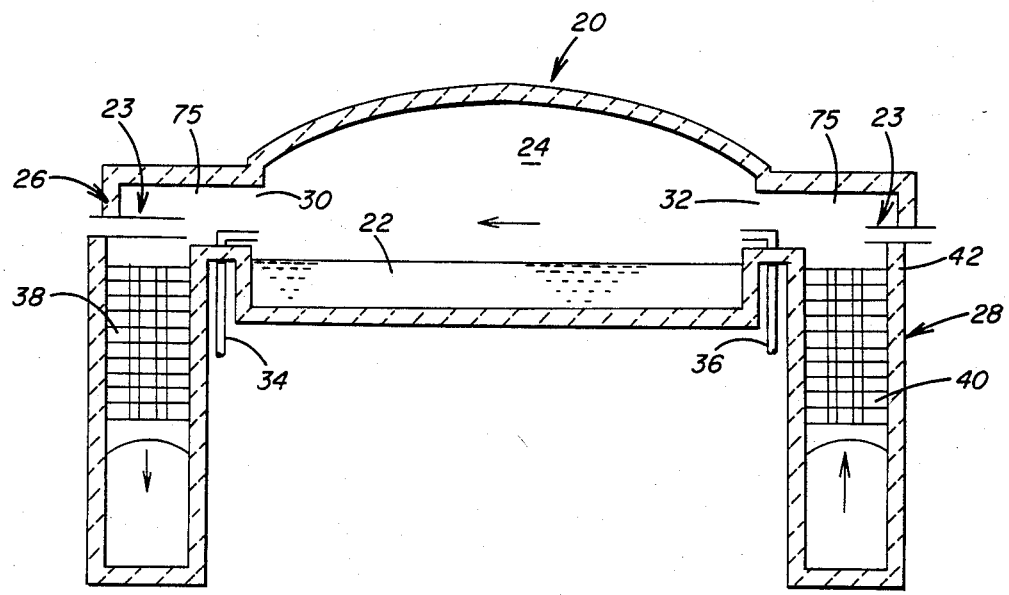
FIG. 1 is a cross-sectional, end elevational view of a regenerative glass melting and/or fining furnace.

The regenerative furnace arrangement 20, shown in FIG. 1, is typical of the melting furnaces used in the flat glass industry. It should be understood that such a furnace is being described as an illustrative example and that the invention is applicable to regenerative furnaces, recuperators, regenerators of other types of and/or other furnaces. As shown in FIG. 1, a pool of molten impartially melted glass 22 is contained in melting zone 24 which also serves as a combustion chamber. Regenerators 26 and 28 flank the combustion chamber 24 an communicate therewith by a plurality of burner ports 30 and 32 respectively. Fuel for combustion is supplied by pipes 34 or 36. Air for combustion passes upwardly through a regenerator 26 or 28 where it is preheated by passing over a hot gas pervious refractory brick work checker packing bed 38 or 40 and then through port 30 or 32 where it combines with fuel from the pipe 34 or 36, respectively, at the mouth of the port. Flames issue a considerable distance into the combustion chamber 24 and resultant hot exhaust gases pass through the port 32 or 30 and into the opposite regenerator 28 or 26 where the exhaust gases heat the refractory packing bed 40 or 38, respectively. The mode of operation, as shown in FIG. 1, is an intake or firing cycle with respect to the regenerator 28 and an exhaust cycle with respect to the regenerator 26. After several minutes of operation, the flows are reversed so that the refractory packing bed 38 of the regenerator 26 serves to preheat combustion air and flames issue from left to right from the port 30 toward the port 32. The regenerator 28 would then be in an exhaust cycle. After several minutes, the direction of flows are again reversed to that shown in FIG. 1 and so on. A complete discussion of a regenerative furnace of a flat glass making apparatus is found in U.S. Pat. No. 4,047,560 which teachings are hereby incorporated by reference.

Figure 2:
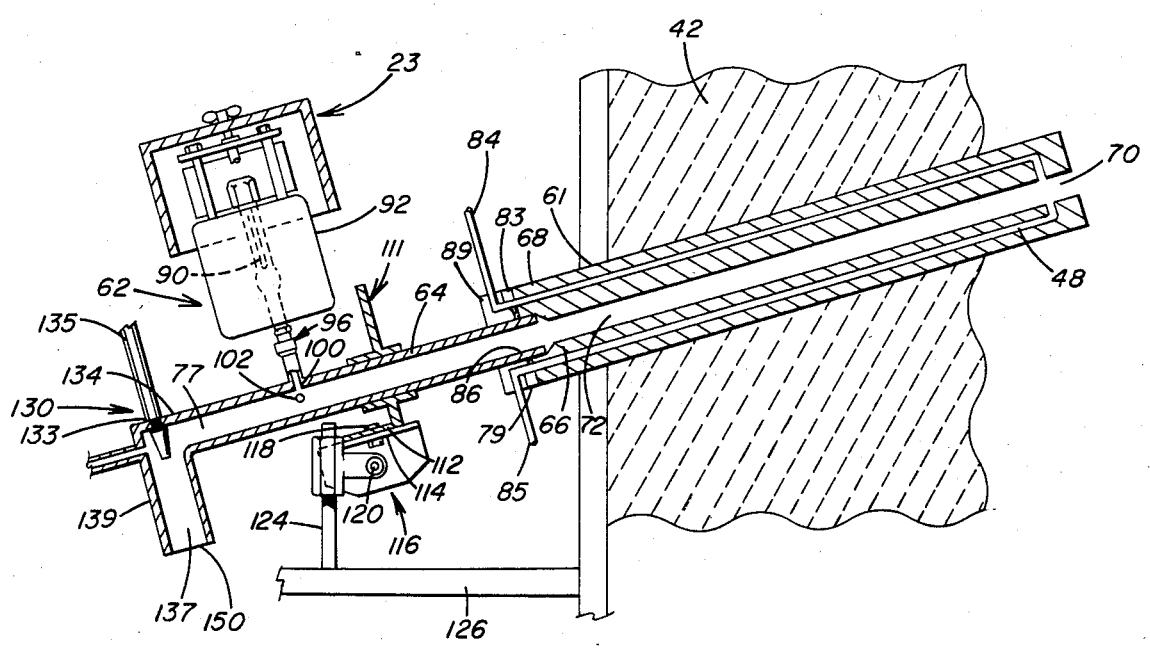
FIG. 2 is an isolation, cross-sectional, side elevational view of an apparatus for analyzing furnace interior atmosphere, incorporating features of the invention.

Referring additionally to FIG. 2, the discussion will now be directed to a suitable device 23 for monitoring or analyzing the atmosphere of the regenerative furnace 20. Although the present invention, as will be discussed later herein, has been used in actual practice with the device 23, which is essentially similar to the analyzing apparatus taught in U.S. Pat. No. 4,358,305, it should be understood that the type of device used in conjunction with the instant invention to monitor an atmosphere, e.g., the interior atmosphere of the regenerative furnace 20, is not limiting to the invention.

The analyzing device 23 includes a gas analyzing assembly 62 connected to an open-ended conduit 64 having its end 66 nearest outside wall 42 of either regenerator 26 or 28 mounted in an adaptor block 68 which is partially mounted in a hole 61 provided through the outside wall 42 of the regenerator 26 or 28. In actual practice, the hole 61 is located above the refractory brick packing bed 38 or 40, respectively, although it should be understood that the location of the hole 61 is not limiting to the invention, e.g., the hole 61 could suitably be placed below the packing bed 38 or 40. The adaptor block 68 is preferably made of a material capable of withstanding the elevated temperatures (e.g., up to and greater than about 2552° F. (1400° C.)) and hostile atmosphere in the regenerative furnace 20. In the actual practice of this invention, the refractory adaptor block 68 was constructed of a castable alumina refractory material sold under the trademark Purotab ®. Another suitable refractory material, among others, that can be used in making the adaptor block 68 is a beta alumina material sold under the trademark Monofrax ®. The invention is practiced with the adaptor block 68 having the dimensions 6"×6"×36" (15.24 cm.×15.24 cm.×91.44 cm.). The block 68 has a ¾ inch (1.905 cm.) diameter bore 70 or gas sample passageway 70 having a chamfered outer mouth 72 for receiving the end 66 of the conduit 64 or gas sample line 64. The invention is practiced with the adaptor block 68 extending outwardly through the hole 61 of the outside wall 42 or target wall 42 of the regenerator 26 or 28, a distance of about 2 inches (5.08 cm.) and extending about 16 inches into the interior of the upper plenum 75 of the regenerator 26 or 28, with the remainder of the block 68 being sealably mounted, e.g., by a refractory cement, within the hole 61 of the target wall 42, which has a cross-sectional thickness of 18 inches (27.72 cm). The type of adaptor block 68 used and its dimensions are not limiting to the invention.

The gas sample line 64 used in the practice of this invention is an approximately 2 feet (0.61 meters) long stainless steel conduit having a 1½ inch (3.81 cm.) diameter bore 77 or gas sample line bore 77. The type of gas sample line 64 used and its dimensions are not limiting to this invention. The inner end 66 of the gas sample line 64 is securably joined/connected to the chamfered outer mouth 72 of the block 68 bore 70 by any suitable material capable of withstanding the temperature and chemistry of the regenerative furnace 20 atmosphere with minimal deterioration. In practice, a refractory cement is used.

A cooling support or conduit 48 is conveniently mounted in the adaptor block 68. The support or conduit 48, which is made of stainless steel or any other convenient strong and durable material, provides structural stability to the block 68 to counteract cantilever forces acting on the block 68 when mounted over the packing 38 or 40 in the regenerators 26 or 28, respectively. These cantilever forces, if not minimized or eliminated, can cause shearing of the block 68. Further, by minimizing or eliminating these cantilever forces, the gas sample passageway 70 can be further extended into the flow of exhaust gases being monitored, thereby minimizing the dilution of the exhaust gas sample due to ambient air or tramp oxygen seepage into the regenerator 26 or 28 through the target wall 42, which sample dilution can adversely affect the accuracy of the determination of oxygen content in the exhaust gases. The support or conduit 48 also provides for moving a cooling medium, e.g., water, through the block 68 to prevent thermal damage to the block 68 to extend the usable life thereof, e.g., as is taught in U.S. Pat. No. 4,338,117 issued to Savolskis et al.

A sealing flange and gasket assembly 79 can be mounted to the outer face 83 of the target wall 42 of the regenerator 26 or 28 in surrounding relationship to inlet portion 84 and outlet portion 85 of the conduit 48 and in surrounding relationship to inner end portion 86 of the gas sample line 64, to form an airtight seal at the jointure of the gas sample line 64 and the adaptor block 68. The flange and gasket assembly 79 preferably includes a gasket 88 pressed against the outer face 83 of the adaptor block 68 by a flange 89 attached to, e.g., bolted to the outer face 83. This installation feature minimizes or prevents the possibility of ambient air intrusion into the gas sample line bore 77, which intrusion could, if not prevented or minimized, adversely affect the accuracy of the determination of oxygen content in the exhaust gases. The gasket 88 and flange 89 are each preferably made of a material which is impervious to air and gas penetration and which can withstand the elevated exhaust gas temperatures. Suitable flange materials are stainless steel and mild steel, although the type and composition of the flange and gasket assembly 79 is not limiting to the invention.

The gas sample line 64 can also be encased by a sleeve (not shown), insulation (not shown), or any other suitable means to reduce heat loss of the sample as it passes through the gas sample line 64 bore 77, e.g., in accordance with the teachings of U.S. Pat. No. 4,358,305, which teachings are herein incorporated by reference.

The gas analyzing assembly 62 is not limiting to the invention and any convenient type for analyzing a gas sample may be used in the practice of the invention. Referring additionally to FIG. 3, the invention is practiced using an oxygen sensor cell 90 mounted in a cell housing 91 which is mounted in an oven 92. The cell housing 91 is connected at one end to convection loop portion 94 and at the other end to convection loop portion 95 of convection loop 96. The other end of the convection loop portion 94 is connected at 100, i.e., ingress hole 100, to the gas sample line 64, and the other end of the convection loop portion 95 is connected at 102, i.e., egress hole 102 to the gas sample line 64. Although not limiting to the invention, the ingress hole 100 and the egress hole 102, are adjacent one another to minimize pressure difference between the gas sample flowing into and out of the convection loop 96 and the cell housing 91 so that the heated sample moves past the sensor cell 90 by convection, as will hereinafter be more fully developed. The sensor 90 used in the practice of the invention is of the type sold by Thermox Company, Type WDG-III and is preferably mounted in the oven cell 90 at a constant temperature for the gas being analyzed, e.g., at hotter than about 1200° F. (650° C.) for oxygen and hotter than about 1400° F. (760° C.) for combustible exhaust gases.

With reference to FIG. 2, the analyzing device 23 can be securely supported in any convenient manner. For example, the gas sample line 64 is mounted to leg 110 of an angle iron 111 with other leg 112 secured to leg 114 of an angle iron 116 by bolt assembly 118. The angle iron 116 is secured to pipe 120 rotatably mounted and secured on pipe 124. The pipe 124, in turn, is mounted on rigid member 126 secured to the superstructure of the regenerator 26 or 28. As can now be appreciated, the invention is not limited to the position of the gas sample line 64 relative to the target wall 42 of the regenerator 26 or 28, nor to the supporting means employed.

The discussion will now be directed to the principal teachings of the invention. Because the pressure differential between the atmosphere of the regenerator 26 or 28 interior and the ambient atmosphere outside of the regenerator 26 or 28 is negative, during the exhaust cycle, some means is necessary to draw or induce a sample portion of the exhaust gases from the interior of the regenerator 26 or 28 through the gas sample passageway 70 of the adaptor block 68, and thenceforth, through the gas sample line 64 bore 77 and the convection loop 96. Referring now to FIGS. 2 and 3, there can be seen aspirating facilities 130 of the present invention suitable for drawing exhaust gas sample portions through the passageway 70 and the bore 77.

The aspirating facilities 130 preferably include an aspirator aperture 133 provided through an outer end portion 134 of the gas sample line 64 downstream from the egress hole 102 and preferably at some substantial distance, e.g., ¾ inch (1.91 cm) therefrom, although this is not limiting to the invention. In the practice of the invention, the aspirator aperture 133 is about ⅛ inch (0.3175 cm) in diameter and is fluidly connected to an aspirator air pipe 135 of compatible diameter, which is fluidly connected to a source of pressurized fluid, e.g., compressed or pressurized air, (glass making factory air pressure is used in the actual practice of the invention). The aspirator air pipe 135 is made of stainless steel in the practice of the invention but can suitably be made of any convenient material. The aspirator aperture 133 is preferably disposed/located diametrically opposite or opposite a central portion of bore 137 of bent portion 139 of the gas sample line 64. The gas sample line 64 is bent at a 90° angle in the practice of the invention, although any other convenient angle can suitably be employed in the practice of the invention, as will hereinafter be appreciated; or the aspirator air pipe 135 can be bent and the bent portion (not shown) can be inserted into a central portion of the gas sample line 64 bore 77 of a straight gas sample line (not shown), in an alternate embodiment of the aspirating facilities 130. Further, the bent portion 139 can suitably be a separate bent member (not shown) fluidly connected to the outer end of a straight gas sample line (not shown).

In operation, when a sample of regenerator 26 or 28 exhaust gas is desired to be inspected for oxygen and/or combustibles content, a stream of pressurized air is directed through the aspirator aperture 133 via the aspirator air pipe 135 and thenceforth through a central portion of the bore 137 of the bent portion 139 of the gas sample line 64, the pressurized air stream exiting at the outer mouth 150 of the bent portion 139 into the ambient atmosphere or into any suitable disposal facility (not shown). The pressurized air stream through the bent portion 139 bore 137 central portion creates a primary partial vacuum within the gas sample line 64 bore 77 and a localized secondary partial vacuum within the bent portion 139 bore 137. The negative air pressure thereby created in the gas sample line 64 draws or induces a sample portion of the exhaust gases flowing through the plenum 75 of the regenerator 26 or 28 into the gas sample passageway 70 of the adaptor block 68 and thenceforth, through the gas sample line bore 77. Prior to exiting the bores 77 and 137, a portion of the gas sample moves by convection into the ingress hole 100 through the convection loop 96 and the cell housing 91 and out of the convection loop 92 by way of the egress hole 102. The sensor cell 90 analyzes the sample passing therethrough for oxygen and/or combustibles content. If the oxygen content as determined by the sensor cell 90 is low, e.g., indicating that excess fuel is being moved through the fuel pipe 34 or 36, the fuel supply is accordingly adjusted to increase combustion efficiency of the regenerative furnace 20. Facilities (not shown) responsive to the oxygen content as determined by the sensor cell 90 could also be provided to automatically adjust the fuel supply through the pipe 34 or 36, e.g., a programmed microprocessor (not shown) or other suitable facilities interfaced with both the sensor cell 90 and fuel supply means (not shown). The air pressure of the pressurized aspirator air in the practice of the invention is 80 psi.

Referring now to FIG. 4, in order to maximize the vacuum created in the gas sample line 64 while simultaneously minimizing the compressed air consumption requirements of the aspirating facilities 130, and significantly reducing the noise level, relative to open jets, an air flow amplifier 170, preferably of the type sold by Vortec Corporation of Cincinatti, Ohio, under their trademark flo-gain ®, nozzle, is fluidly connected to the aspirator aperture 133 so as to extend transversely across the gas sample line 64 bore 77 and slightly therebeyond into a central portion of the bent portion 139 bore 137. The compressed air gains sonic velocity through an adjustable slot 180 provided at an end portion of a copper aspirator tube 182, which is fluidly connected at its opposite end to the aspirator air pipe 135. The compressed air then flows in the direction of the directional flow arrows just over the exterior surface 187 of the truncated, generally cone-shaped, closed-ended nozzle 185, the distance between the flowing air and the surface 187 varying with the setting of the slot 180 selected. A micrometer dial 190 allows adjustment of the slot 180 without the use of shims or gauges. Induction and entrainment of the regenerator 26 or 28 exhaust gases take place outside the flo-gain ® nozzle 185. The aspirator facilities 130 further include a gas sample line clean-out hole 200 provided through wall portion 202 of the bent portion 139 of the gas sample line 64 opposite the gas sample line 64 bore 77. A plug 206 is inserted in the clean-out hole 200 during operation of the invention. However, during a firing cycle of the regenerator 26 or 28, the plug 206 can be removed and a blast of pressurized air shot/directed through the bore 77 to force undesirable exhaust gas residue and/or ambient air buildup out of the inner end of the gas sample passageway 70 and into the regenerator 26 or 28 interior. If the sample line bore 77 is not periodically or regularly cleaned out, exhaust gas residue and/or ambient air buildup will distort the operation of the oxygen sensor 91, resulting in inaccurate oxygen content determinations/measurements. The plug 206 can be made of iron, steel or any other convenient material and is preferably threadably mated to the clean-out hole 200 for easy screw-in insertion and screw-out removal, although the type of plug 206 used is not limiting to the invention. In the actual practice of the invention, an 80 psi blast of compressed air of a 15-30 second duration once a day sufficed to prevent any buildup or accumulation of exhaust gas residue in the bore 77. However, it would be preferable to additionally or alternatively provide an automatic sample line 64 bore 77 clean-out device (not shown) which would operate in synchronicity with the cyclic operation of the regenerative furnace 20 to automatically blow a sufficient amount of pressurized fluid, e.g., compressed air, through the bore 77 to prevent any residual gas buildup which could adversely affect the accuracy of the sensor cell 90 readings. For example, the automatic clean-out device (not shown) as above-described could include an air supply means (not shown) functionally connected to a timer (not shown) which is preset in accordance with the cycle time of the furnace 20. Further, many other alternative purging and/or scrubbing means to ensure that the gas sample line 64 and the gas passageway 70 remain free and substantially devoid of any substances or residue which may dilute exhaust gas samples being monitored will readily become apparent to those in the art, and are encompassed within the spirit and scope of the present invention.

As can now be appreciated, the present invention is not limited to the above-described illustrative examples and embodiments, but should have its scope determined in accordance with the following claims.

What is claimed is:

1. A method for monitoring the interior atmosphere of a furnace wherein the pressure of the furnace interior atmosphere is less than that of the furnace exterior atmosphere, including the steps of:

providing a fluid flow conductor communicating at one end with the furnace interior atmosphere and at its opposite end with the furnace exterior atmosphere;

creating at least a partial vacuum within said fluid flow conductor to aspirate a portion or sample of the furnace interior atmosphere through said fluid flow conductor to the furnace exterior atmosphere;

moving at least a portion of said sample past said analyzing means; and analyzing said sample to monitor said sample with respect to its content.

2. The method as set forth in claim 1, wherein said analyzing step includes determining oxygen content in said sample, and wherein it further includes the step of controlling oxygen content in the chamber atmosphere in response to said analyzing step.

3. An apparatus for monitoring the interior atmosphere of a furnace, including:

means disposed exteriorly of the furnace for analyzing a portion of the furnace interior atmosphere having a pressure less than that of the furnace exterior atmosphere, said portions being defined as a sample; and means for aspirating said sample from the furnace interior to said analyzing means for analysis of said sample, said aspirating means including:

a fluid flow conductor communicating at one end with the furnace interior atmosphere and at its opposite end with the furnace exterior atmosphere;

means for fluidly interconnecting said analyzing means and said fluid flow conductor; and means for creating at least a partial vacuum within said fluid flow conductor for inducing said sample to flow from the furnace interior through said fluid flow conductor to the furnace exterior atmosphere, at least a portion of said sample being moved past said analyzing means for analysis of said sample.

4. The apparatus as set forth in claim 3, wherein said fluidly interconnecting means include a convection pipe loop having a sample entrance end and a sample exit end, said at least a portion of said sample being convected through said convection pipe loop, prior to exiting said fluid flow conductor, and past said analyzing means for analysis of said sample.

5. The apparatus as set forth in claim 4, wherein said fluid flow conductor includes:

a refractory adaptor block having a sample passageway extending between and through first and second ends of said adaptor block;

means for mounting said adaptor block in an outside wall of said furnace at a location such that said sample passageway communicates at one end with said furnace interior atmosphere; and a sample conduit fluidly connected at one end with the opposite end of said sample passageway, and at its opposite end with said furnace exterior atmosphere, and intermediately to said convection pipe loop.

6. An apparatus for monitoring the interior atmosphere of a regenerative glassmaking furnace, including:

means disposed exteriorly of the furnace for analyzing a portion of the furnace interior atosphere defined as a sample;

means for aspirating said sample from the furnace interior to said analyzing means for analysis of said sample, said aspirating means including:

a refractory adaptor block having a sample passageway extending between and through first and second ends of said adaptor block;

means for mounting said adaptor block in an outside wall of the furnace at a location such that said sample passageway communicates at one end with the interior atmosphere of the furnace;

a sample conduit fluidly connected at one end with the opposite end of said sample passageway, and at its opposite end with the furnace exterior atmosphere;

a convection pipe loop having a sample entrance end and a sample exit end disposed in fluid communication with said sample conduit at spaced points intermediate said ends of said sample conduit, at least a portion of said sample being convected through said convection pipe loop, prior to exiting said sample conduit, and past said analyzing means for analysis of said sample; and a vacuum creating means, including:

a portion of said sample conduit located downstream of said convection pipe loop, wherein said portion is bent so as to project substantially laterally with respect to the other or unbent portion of said sample conduit;

an aperture provided through a wall of said sample conduit opposite a central portion of the interior of said bent portion; and means for directing pressurized fluid from a source of pressurized fluid through said aperture and thence through said central portion of said bent portion interior to said furnace exterior atmosphere, to thereby create at least a partial vacuum within said sample conduit; and wherein the pressure differential between the furnace interior and the furnace exterior is negative.

7. The apparatus as set forth in claim 6, wherein said directing pressurized fluid means includes an aspirator conduit fluidly interconnecting said pressurized fluid source with said bent portion interior central portion through said aperture.

8. The apparatus as set forth in claim 7, wherein said directing pressurized fluid means further includes means for amplifying the flow of said pressurized fluid through said bent portion interior central portion, to maximize the vacuum created in said sample conduit and to minimize pressurized fluid consumption.

9. The apparatus as set forth in claim 8, wherein said amplifying means includes:

an elongated tube having an unsealed end portion fluidly connected to said aspirator conduit and a diametrically decreasing tapered, sealed opposite end portion; and a slot provided through said tube around at least a portion of the periphery thereof between said end portions thereof for directing said pressurized fluid therethrough and thenceforth along at least a portion of said tapered, sealed opposite end portion in close relation thereto to establish a fluid flow pattern corresponding to the shape of said opposite end portion, to thereby entrain a portion of the interior atmosphere of said sample conduit to flow therewith through said bent portion interior to said furnace exterior atmosphere, to thereby create at least a partial vacuum within said sample conduit.

10. The apparatus as set forth in claim 8, wherein said amplifying means includes a flow amplifier of the type sold by Vortec Corporation of Cincinatti, Ohio under their trademark flo-gain ® nozzle.

11. The apparatus as set forth in claim 6, wherein it further includes means for minimizing material buildup and sample residue within the interior of said sample conduit to minimize distortion of said analysis performed by said analyzing means due to dilution of said sample by material buildup and sample residue within said sample conduit.

12. The apparatus as set forth in claim 11, wherein the furnace is a regenerative furnace characterized by a pair of opposed first and second regenerators flanking and fluidly communicating with a combustion chamber, wherein each regenerator has an upper plenum communicating with the combustion chamber, a lower plenum communicating with the furnace exterior atmosphere, and a refractory packing bed interposed therebetween, wherein air for combustion passes upwardly through said first regenerator where it is preheated by passing over said refractory packing bed of said first regenerator and then into said combustion chamber, where it combines with fuel in said chamber, whereupon flames issue into said chamber and hot exhaust gases issue into said second regenerator, the hot exhaust gases passing over and heating said refractory packing bed of said second regenerator, the mode of operation, defined as a firing cycle with respect to said first regenerator and an exhaust cycle with respect to said second regenerator, being cyclically reversed.

13. The apparatus as set forth in claim 12, wherein the furnace interior atmosphere is the interior atmosphere of said first regenerator or said second regenerator when said first or said second regenerator, respectively, is in an exhaust cycle, and wherein further, said sample includes a portion of said hot exhaust gases issuing from said combustion which takes place within said chamber.

14. The apparatus as set forth in claim 13, wherein said minimizing means includes means for directing pressurized fluid from a pressurized fluid source through the interior of said sample conduit, and thenceforth through said sample passageway into said first or said second regenerator interior atmosphere during the firing cycle of said first or said second generator.

15. The apparatus as set forth in claim 14, wherein the jointure between said sample conduit and said sample passageway includes refractory cement and is fluidly sealed by a flange and gasket assembly mounted to the furnace exterior face of said adaptor block.

16. The apparatus as set forth in claim 15, wherein said analyzing means includes a sensing device for quantitatively monitoring presence of a selected gas or gases in said sample.

17. The apparatus as set forth in claim 16, wherein said selected gas is oxygen and said regenerative furnace is of the type used for melting and/or fining glass.

18. The apparatus as set forth in claim 17, wherein it further includes means for controlling oxygen content in the chamber in response to said analyzing means.

* * * * *